(12) United States Patent
Shanbrom

(10) Patent No.: US 6,881,731 B1
(45) Date of Patent: Apr. 19, 2005

(54) ENHANCERS FOR MICROBIOLOGICAL DISINFECTION

(75) Inventor: Edward Shanbrom, Santa Ana, CA (US)

(73) Assignee: Shanbrom Technologies, LLC, Ojai, CA (US)

( * ) Notice: Subject to any disclaimer, the term of this patent is extended or adjusted under 35 U.S.C. 154(b) by 0 days.

(21) Appl. No.: 09/694,178

(22) Filed: Oct. 23, 2000

(51) Int. Cl.$^7$ .................. A61K 31/33; A01N 43/02
(52) U.S. Cl. ........................... 514/183; 514/450
(58) Field of Search .................. 514/183, 450; 424/667

(56) References Cited

U.S. PATENT DOCUMENTS

| | | | | |
|---|---|---|---|---|
| 4,025,654 A | * | 5/1977 | Farhadieh | 514/656 |
| 5,459,030 A | * | 10/1995 | Lin et al. | 435/2 |
| 5,656,591 A | * | 8/1997 | Tomita et al. | 514/6 |
| 5,660,731 A | * | 8/1997 | Piechocki et al. | 210/669 |
| 5,875,799 A | * | 3/1999 | Petrus | 132/323 |
| 5,985,260 A | * | 11/1999 | Shanbrom | 424/78.08 |

FOREIGN PATENT DOCUMENTS

| WO | 8900006 | * | 1/1989 |
|---|---|---|---|
| WO | 9822151 | * | 5/1998 |

OTHER PUBLICATIONS

Brown et al, The stability of suspensions prepared from solid dosage froms, 1976, J. Clin. Pharm., vol. 1 No. 1, pp. 29–37.*

* cited by examiner

*Primary Examiner*—Alton Pryor
(74) *Attorney, Agent, or Firm*—Liner, Yankelevitz, Sunshine and Regenstreif, LLP

(57) ABSTRACT

Simple carboxylic acids, in particular dicarboxylic acids such as citric acid shows an unexpected ability to enhance the antimicrobial power of a wide range of disinfectant and/or antibiotic agents. As little as 1% citrate greatly enhances the ability of antibiotics to kill or inhibit a wide range of bacterial species including antibiotic resistant strains. Citrate alone is effective in preventing bacterial growth in platelet concentrates and in red blood cell suspensions. Effective concentrations of citrate cause little if any damage to blood cells. Besides enhancing the power of antibiotics citrate also enhances the antimicrobial properties of disinfectant organic dyes such as crystal violet and methylene blue. In addition citrate enhances the antimicrobial properties of polyphenols of plant origin. Iodine-based disinfectants are also enhanced without enhancing protein denaturation.

1 Claim, No Drawings

ENHANCERS FOR MICROBIOLOGICAL DISINFECTION

BACKGROUND OF THE INVENTION

1. Area of the Art

The present invention deals with disinfection in the medical area and in particular agents that greatly potentiate the activity of known antimicrobial and disinfection agents.

2. Description of the Prior Art

It has long been known that various chemical agents can be used to kill or otherwise limit the growth of infectious agents such as bacteria and viruses. Many of the initial disinfecting materials were active, even caustic, chemicals such as the "carbolic acid" (phenol) used by Lister in the early days of the germ theory of disease. In the last century anti-infective agents of biological origin such as penicillin, were discovered and widely exploited. Antibiotic drugs used to treat infectious diseases have proliferated and were used liberally in developed countries following the Second World War. These drugs are widely used not only to treat disease but to obtain enhanced growth of farm animals living under often substandard "factory farm" conditions. As a result of this sort of excessive use and misuse by patients, many new, antibiotic resistant organisms have evolved. Drug companies and researchers are actively seeking new compounds to fight these resistant disease organisms. Most of their research however is targeted at finding single chemical compounds or combinations of chemical compounds that act on these organisms.

Combination therapies have been around for many years as demonstrated in the book "Combination Antibiotic Therapy in the Compromised Host", edited by J. Klastersky and MJ Staquet, New York, Raven Press, 1982. Other more recent work on combination therapies is the work done with fluoroquinolones (Meyer, RD, J. Antimicrob. Chemother., 1991, 28, 623). The general idea of combination therapy is to develop a synergistic drug combination or to somehow enhance the activity of a known antibiotic or even some other disinfectant or anti-infective agent. In many instances combination therapies are sought as ways to overcome drug resistant disease organisms. For example, penicillin, the first widely used antibiotic, has now lost much of its usefulness due to resistant organisms. One form of penicillin resistance involves the production of penicillin destroying enzymes (penicillinase) by disease organisms. Therefore, one type of combination therapy is to combine compounds that inhibit penicillinase with the penicillin. This approach can largely restore the resistant organism's sensitivity to penicillin.

Antibiotics are natural biological compounds often of bacterial or fungal origin. Many of our drugs are of plant origin. Therefore, it is hardly surprising that much research is now being conducted in the area of the antimicrobial qualities of herbs, fruit extracts and other materials of plant origin. For the most part, companies and researchers are studying the efficacy of extracts of plant materials, alone or the efficacy of specific purified molecules of the plant material extracts. A series of patents by Walker et al. (U.S. Pat. Nos. 5,474,774, 5,525,341, 5,646,178, and 5,650,432) describe the isolation and purification of specific compounds from cranberry for use as antimicrobials. In particular it was demonstrated that these agents interfere with the adhesion of bacteria to the endothelial cells of the urinary tract. The present inventor has purified antimicrobial colored compounds from cranberry and other plant materials. These compounds actually have bacteriostatic as well as bactericidal and virucidal activities as described in U.S. Pat. No. 6,093,401.

The present inventor has long had an interest in disinfecting blood and blood products. Out of this interest the just mentioned interest in antimicrobial plant products developed. From his many years of experience with blood fractionation and production of blood products the present inventor was extremely familiar with the use of various chemicals as anticoagulants in blood and blood products. Common anticoagulants are EDTA, heparin, oxalic acid, citric acid and their salts. Of these all but heparin function primarily by reducing the level of calcium ions. One of the inventor's experiments aimed at disinfecting blood plasma inadvertently removed the citric acid (actually sodium citrate) used as an anticoagulant with the resulting precipitation (coagulation) of the plasma. Attempts were made to overcome this problem through the addition of extra citric acid. This resulted in the present discovery of the unexpected properties of citric acid, which forms the substance of the present invention.

It should be appreciated that there is a pressing need for the disinfection of blood and blood products used for transfusion and other medical therapies. In the first place collected blood is virtually always contaminated with bacteria commonly present on the skin of the blood donor. The needle used for blood donation picks up these organisms and contributes them to the donated blood. These bacteria especially cause problems with platelet concentrates whose useful life is currently limited to five days because of bacterial growth whereas the biologically useful life of the concentrates is at least several additional days. With the current shortages of donated blood this rapid outdating of platelet concentrates is especially troublesome.

Another reason for disinfection is the one that occurs to most people concerned with blood safety-namely blood borne disease. When the blood donor is infected with viral or other disease agents, the infection may be spread through blood transfusion or receipt of blood products made from infected blood. Currently a detergent-based process, originated by the present inventor, is used to inactivate many viruses present in blood plasma. This results in safer plasma and blood products made therefrom. However, detergents cannot be used on whole blood because they damage or destroy blood cells. Thus, there is a great need for methods to disinfect whole blood and cellular fractions thereof. Further, the current detergent process does not inactivate all dangerous blood borne viruses. Therefore, there is also a pressing need for improved disinfection of plasma.

The present inventor has discovered that increasing the concentration of citrate to levels higher than those usual for anticoagulation results in significant decreases in bacteria and bacterial growth in blood and blood fractions. Further, citrate shows an unexpected synergistic effect when combined with a wide variety of antibiotics, antimicrobials and disinfecting agents including iodine and natural plant products such as those from grape of cranberry. Citrate has been used in dental rinses and is widely used as an anticoagulant and a buffering agent in foods, pharmaceuticals and cleaning materials. However, the antimicrobial synergistic effects of citrate have hitherto not been appreciated.

SUMMARY OF THE INVENTION

Simple carboxylic acids, in particular dicarboxylic acids such as citric acid shows an unexpected ability to enhance the antimicrobial power of a wide range of disinfectant and/or antibiotic agents. As little as 1% citrate greatly enhances the ability of antibiotics to kill or inhibit a wide range of bacterial species including antibiotic resistant strains. Citrate alone is effective in preventing bacterial growth in platelet concentrates and in red blood cell suspensions. Effective concentrations of citrate cause-little if any damage to blood cells. Besides enhancing the power of antibiotics citrate also enhances the antimicrobial properties of disinfectant organic dyes such as crystal violet and methylene blue. In addition citrate enhances the antimicrobial properties of polyphenols of plant origin. Iodine-based disinfectants are also enhanced without enhancing protein denaturation.

DETAILED DESCRIPTION OF THE INVENTION

The following description is provided to enable any person skilled in the art to make and use the invention and sets forth the best modes contemplated by the inventor of carrying out his invention. Various modifications, however, will remain readily apparent to those skilled in the art, since the general principles of the present invention have been defined herein specifically to provide a method to greatly enhance the antimicrobial effects of antibiotics, plant natural products and disinfecting chemicals.

Citrate Effect on Platelets and Red Cells

Two 50 ml aliquots of platelet rich plasma were prepared by centrifugation. One of the samples was brought to 2% by weight citric acid. As explained above, human platelet concentrates are ordinarily contaminated with human skin bacteria. These bacteria grow even if the platelet concentrates are kept at low temperatures. Such bacterial growth significantly shortens the useful life of these platelet preparations. In this experiment the solution were incubated on a rotator at room temperature. Such conditions are ideal for preservation of platelet function but are also excellent for bacterial growth. Samples were removed each day and counted to determine the state of the platelets. It was already determined in other experiments that these levels of citrate were very effective in killing or inhibiting bacteria. The question was whether the citrate would harm the platelets.

| Treatment Day | Platelet Count (per ml) (control) | Platelet Count (per ml) (2% Citrate) |
|---|---|---|
| 1 | $4.0 \times 10^5$ | $4.2 \times 10^5$ |
| 2 | $4.2 \times 10^5$ | $4.3 \times 10^5$ |
| 3 | $3.7 \times 10^5$ | $4.0 \times 10^5$ |
| 4 | $3.8 \times 10^5$ | $3.7 \times 10^5$ |
| 5 | $3.7 \times 10^5$ | $3.7 \times 10^5$ |
| 6 | $2.7 \times 10^5$ | $3.1 \times 10^5$ |

These results indicate that platelets do not show obvious damage after exposure to 2% citrate. The platelet counts appear to be about the same either with or without the citrate. Over time the number of platelets gradually decreases. However, the decrease is slower in the presence of citrate suggesting that this agent may actually stabilize or preserve the platelets. Other studies have shown that platelets maintain adequate function for at least seven days, but solutions are not used beyond five days because of excessive bacterial growth.

Similarly, 2% citrate does not appear to damage red blood cells (RBCs). Normally red blood cells are very sensitive to added agents. The damage to the red cell membrane can be observed as hemolysis (leakage of hemoglobin from the cells) or as an increase in potassium ($K^+$) or lactate dehydrogenase (LDH) both of which leak out of damaged red cells. In this experiment blood sample either with or without citrate (2%) were sampled over a seven-day period.

| Day | Hemolysis | $K^+$ ($\mu$g/ml) | LDH (IU/ml) |
|---|---|---|---|
| Control | | | |
| 1 | — | 3.2 | 100 |
| 2 | — | 3.2 | 101 |
| 3 | — | 3.3 | 100 |
| 4 | — | 3.2 | 102 |
| 5 | — | 3.4 | 101 |
| 6 | — | 3.4 | 103 |
| 7 | slight | 3.5 | 105 |
| 2% Citrate | | | |
| 1 | — | 3.2 | 101 |
| 2 | — | 3.3 | 100 |
| 3 | — | 3.3 | 100 |
| 4 | — | 3.3 | 100 |
| 5 | — | 3.2 | 101 |
| 6 | slight | 3.5 | 106 |
| 7 | slight/moderate | 3.8 | 110 |

These results indicate that increased citrate may have a very slight effect on red cells (increased because 0.5% citrate is commonly used as an anticoagulant). However, this is much less harmful than many other agents that have been used in an attempt to disinfect red cells. Therefore, citrate can be combined with other agents to disinfect red cells with increasing the damage to the red cells. An important point is that the added citrate can be readily reduced or removed with anion exchange materials.

Citrate and Antibiotics

The effects of 5% and 8% (weight by volume) of citric acid on bacteriological broth was investigated. In each case the pH of the broth was adjusted with NaOH to bring it into normal growth ranges if necessary. The amount of growth is rated from minimum (+) to maximum (4+). If no growth occurred, the treatment is marked 'NG'. Each broth sample was inoculated with 1×103 organisms of vancomycin resistant *Enterococcus*. The inoculated broth was incubated for 2 hr at 35° C. for 2 hr and then plated on growth media, which was allowed to incubate overnight under optimal growth conditions.

| Medium | Level of Growth |
|---|---|
| Broth alone | 4+ |
| Broth + 5% citrate | 4+ |
| Broth + 8% citrate | 3+ |
| Broth + 250 $\mu$g/ml vancomycin | 3+ |
| Broth + 5% citrate + 250 $\mu$g/ml vancomycin | 1+ |
| Broth + 8% citrate + 250 $\mu$g/ml vancomycin | NG |

These results show that either 8% citrate or 250 $\mu$g/ml vancomycin alone cause some inhibition of bacterial growth. This level of the vancomycin was selected because it would be sufficient to completely inhibit non-resistant bacteria. The combination of citrate with the vancomycin completely inhibits the resistant bacteria. This shows that the synergistic effect of vancomycin with citrate is sufficient to overcome bacterial resistance.

Citrate is also effective with other combinations of bacteria/antibiotics. In the following experiment a suspension of 1×10³ cell/ml of *Klebsiella pneumoniae* was prepared in trypsicase soy broth. Ten ml aliquots were treated with citrate and/or antibiotics. After a two hr incubation at room temperature, 0.1 ml samples of each treatment were spread on soy trypsicase broth agar and incubated overnight at 35° C. The plates were then scored for bacterial growth with the following results:

| Medium | Level of Growth |
| --- | --- |
| Broth alone | 4+ |
| Broth + 2% (by wgt.) trisodium citrate | 3+ |
| Broth + 8% citrate | 3+ |
| Broth + 25 µg/ml ampicillin | 2+ |
| Broth + 2% trisodium citrate + 25 µg/ml ampicillin | NG |

These results indicate that the antibiotic-citrate effect extends to more than a single antibiotic-bacterial species combination. Additional experiments (data not shown) have demonstrated that citrate enhances the activity of a wide range of antibiotics against a large number of bacterial species and strains both wild types and antibiotic resistant types.

Citrate Enhancement of Antimicrobial Pigments

It has long been known that a variety of organic dyes show antimicrobial properties. Much study was expended on these compounds prior to the discovery of modern antibiotics. Some of the "disinfectant" dyes such as crystal (gentian) violet still enjoy some use. I have discovered in other work that a combination of two of the disinfectant dyes—namely crystal violet plus methylene blue—are especially effective at preventing growth of a wide range of bacteria. I have also previously discovered that the polyphenol pigments which precipitate during the aging of grape wine (called lees) also exhibit antibacterial properties. The following experiment was carried out to see if the synergistic properties of citrate extend to such antimicrobial pigments. There is some indication in the literature that ascorbic acid may also show some synergistic properties with such antimicrobials. Therefore, sodium ascorbate was also tested.

An aqueous solution of equal weights of methylene blue and crystal violet (0.0057% of each) was prepared. Also an aqueous suspension of red wine lees (0.25%) was also prepared. Treatment solutions were prepared by adding either sodium citrate or sodium ascorbate to 1.5% by weight from a stock solution. Control aliquots contained neither citrate nor ascorbate.

For test purposes each sample was inoculated with 1×10$^4$ cells of either Escherichia coli or Staphylococcus epidermidis. The sample was then incubated at room temperature for 60 min with agitation. At the end of the incubation period the samples were plated onto TSA growth media and incubated overnight at 35° C. The plates were then scored for number of colonies with NG indicating "no growth" and 4+indicating maximal growth.

| Treatment | E. coli | S. epidermidis |
| --- | --- | --- |
| Control | 4+ | 3+ |
| Dye alone | 2+ | 2+ |
| Citrate alone | 1+ | — |
| Dye-citrate | NG | NG |
| Dye-ascorbate | 1+ | 1+ |
| Lees alone | 1+ | 2+ |
| Lees-citrate | NG | NG |
| Lees-ascorbate | 1+ | 2+ |

These results indicate that both the dye mixture and the lees show significant antibacterial properties. When either dye or lees are combined with 1.5% sodium citrate all bacterial cells are killed or prevented from further growth. Ascorbate shows some ability to potentiate the effect of the dye mixture but has no apparent effect on the lees.

Citrate Compared to EDTA

EDTA (ethylenediaminetetraacetic acid) is a calcium chelating anticoagulant that is known to have some antimicrobial activity. Sodium diacetate is another calcium chelating material with known antimicrobial and anticoagulation properties. The chelating agents were compared by incubating suspension of 1×10$^3$ cells/ml of Escherichia coli or Staphylococcus epidermidis in human plasma for 60 min at room temperature for 60 min prior to incubating 100 µl of suspension (potentially 100 cells) under optimal conditions for 12 hrs. Human plasma represents a rich growth medium and heavy bacterial growth is expected. All added compounds are expressed as percent by weight.

| Treatment | Growth S. epidermidis | Growth E. coli |
| --- | --- | --- |
| Control (plasma alone) | 4+ | 4+ |
| 8% Sodium EDTA | — | 3+ |
| 8% Sodium Diacetate | — | NG |
| 8% Sodium Citrate | NG | NG |
| 2% Sodium Citrate | — | 1+ |
| 8% Citric Acid | NG | NG |
| 8% Sodium Oxalate | 3+ | 3+ |
| 8% Sodium Heparin | 3+ | 3+ |

These results that EDTA, sodium oxalate and sodium heparin even at concentration considerably higher than used for anticoagulation shows limited antibacterial properties. At the high level of 8% sodium diacetate completely prevents growth of E. coli. At 8% both sodium citrate and citric acid prevent bacterial growth entirely. At 2% sodium citrate causes considerable inhibition of E. coli. It should be kept in mind that this percentage is still some four times the normal amount used for anticoagulation. Since the anticoagulating ability of both EDTA, oxalate and citrate are related to the ability of these compounds to chelate calcium ions, it seems apparent that the antibacterial effect of citrate is not due to its effect on calcium ions or at least not solely to its effect on calcium ion. Like citrate the diacetate has multiple carboxylic acid groups per molecule.

Citrate Effect on Povidone Iodine

A 50 ml aliquot of 2% (by weight) trisodium citrate in bacterial growth broth was prepared and spiked with Escherichia coli (1×10$^3$ cells/ml). The spiked broth was divided into six 8 ml aliquots. A 25 ml aliquot of spiked broth without citrate was used as a control. The control aliquot was divided into three 8 ml samples. Samples were taken at 30 min, 6 hr and 24 hr while the aliquots incubated at room temperature. For the iodine samples 400 µl of 10% povidone-iodine (PVP-I) was added to the sample 5 min prior to the sampling. The samples were plated on trypsicase soy agar (TSA) and allowed to grow overnight under optimal conditions prior to counting. To review, the 30 min sample were allowed to grow for 30 min. Then PVP-I was added to the appropriate sample and material was removed for plating after 5 min. The 6 hr samples grew for 6 hr prior to the PVP-I addition followed by plating; the 24 hr samples grew for 24 hr prior to PVP-I addition.

| Medium | 30 min | 6 hr | 24 hr |
|---|---|---|---|
| Broth + 2% citrate | 3+ | 4+ | 4+ |
| Broth + PVP-I | 3+ | 3+ | 4+ |
| Broth + 2% citrate + PVP-I | 1+ | NG | NG |

These results suggest that citrate potentiates the killing power of PVP-I and/or cells grown in the presence of citrate were weakened and made more susceptible to the iodine.

Citrate Effect on Iodine Based Viral Inactivation

The following experiments represent a refinement of initial iodine experiments that resulted in the discovery of the citrate effect. The iodine inactivation process is the result of many years of investigations. The general idea is to expose a sample of virally contaminated solution (here human plasma) to a source of active iodine and then remove the iodine before damage is done to delicate proteins. In the case of plasma it is possible to monitor sensitive blood clotting enzymes to check for protein denaturation. The process that has been developed involves using an iodine containing resin to donate iodine to the solution and an iodine/iodide binding resin to remove the iodine and any resulting iodide. A surprising development of this line of research was that repeated passage through a mixed column of iodine donating and iodine/iodide absorbing resin was especially effective at inactivating virus while retaining activity of blood clotting enzymes. That work is now U.S. Pat. No. 6,045,787 which is incorporated herein by reference.

In the present experiment a 1500 ml sample of human plasma was spike with approximately $1 \times 10^6$ particles of Porcine Parvo Virus (PPV) and $5 \times 10^5$ particles of Bovine Viral Diarrhea Virus (BVDV). The plasma was then brought to 8% sodium citrate.

The plasma was then cycled four times through a large column of iodine and iodine capture mixed resin (1:8). After each pass residual iodine ($I_2$) and iodide ($I^-$) were measured using an iodide sensitive electrode (Orion Research Instruments). The electrode reads the iodide concentration directly. Sodium ascorbate was added to each sample to determine iodine concentration. Any increase in iodide reading represented reduction of iodine to iodide by the ascorbate. It was not expected that much if any iodine or iodide would be present because of the large excess of iodine/iodide binding resin in the column.

| Iodide and Iodine per Pass | | |
|---|---|---|
| Treatment | Iodide (ppm) | Iodine (ppm) |
| Control (no column treatment) | 0 | 0 |
| Pass 1 | 0 | 0 |
| Pass 2 | 1 | 0 |
| Pass 3 | 0 | 0 |
| Pass 4 | 0 | 0 |

The concentration of the various viruses was determined using a Viral Endpoint Assay (VEPA). Briefly, samples to be tested were placed on a monolayer of appropriate cells (i.e., host cells for the particular virus). After an incubation period, virus presence was determined by plaque formation. Each sample was tested over a range of serial two-fold dilutions so that the greatest dilution still showing plaque formation could be determined. Viral titer was calculated from this dilution assay using a well known formula.

As had been determined from past research, the column treatment resulted in some type of latent damage to the virus. It was found that holding the sample for up to 24 hrs prior to plating onto a cell culture would result in increased viral inactivation.

| | | | PPV Inactivation | | | | | | | | | | | |
|---|---|---|---|---|---|---|---|---|---|---|---|---|---|---|
| Time | | 1 | 2 | 3 | 4 | 5 | 6 | 7 | 8 | 9 | 10 | 11 | 12 | Titer |
| | control | 4 | 4 | 4 | 4 | 4 | 4 | 4 | 4 | 2 | 0 | 0 | 0 | 6.3 |
| 0 hrs | P1 | 4 | 4 | 4 | 4 | 4 | 4 | 4 | 1 | 0 | 0 | 0 | 0 | 5.4 |
| | P2 | 4 | 4 | 4 | 4 | 4 | 0 | 0 | 0 | 0 | 0 | 0 | 0 | 3.8 |
| | P3 | 4 | 4 | 4 | 2 | 0 | 0 | 0 | 0 | 0 | 0 | 0 | 0 | 2.8 |
| | P4 | 4 | 2 | 0 | 0 | 0 | 0 | 0 | 0 | 0 | 0 | 0 | 0 | 1.4 |
| 6 hrs | P1 | 4 | 4 | 4 | 4 | 3 | 0 | 0 | 0 | 0 | 0 | 0 | 0 | 3.7 |
| | P2 | 4 | 4 | 4 | 2 | 0 | 0 | 0 | 0 | 0 | 0 | 0 | 0 | 2.8 |
| | P3 | 4 | 3 | 0 | 0 | 0 | 0 | 0 | 0 | 0 | 0 | 0 | 0 | 1.6 |
| | P4 | 2 | 0 | 0 | 0 | 0 | 0 | 0 | 0 | 0 | 0 | 0 | 0 | 0.7 |
| 24 hrs | P1 | 4 | 1 | 0 | 0 | 0 | 0 | 0 | 0 | 0 | 0 | 0 | 0 | 1.2 |
| | P2 | 0 | 0 | 0 | 0 | 0 | 0 | 0 | 0 | 0 | 0 | 0 | 0 | 0 |
| | P3 | 0 | 0 | 0 | 0 | 0 | 0 | 0 | 0 | 0 | 0 | 0 | 0 | 0 |
| | P4 | 0 | 0 | 0 | 0 | 0 | 0 | 0 | 0 | 0 | 0 | 0 | 0 | 0 |

| | | | BVDV Inactivation | | | | | | | | | | | |
|---|---|---|---|---|---|---|---|---|---|---|---|---|---|---|
| Time | | 1 | 2 | 3 | 4 | 5 | 6 | 7 | 8 | 9 | 10 | 11 | 12 | Titer |
| | control | 4 | 4 | 4 | 4 | 4 | 4 | 4 | 1 | 0 | 0 | 0 | 0 | 5.4 |
| 0 hrs | P1 | 4 | 4 | 4 | 4 | 0 | 0 | 0 | 0 | 0 | 0 | 0 | 0 | 3.1 |
| | P2 | 4 | 4 | 3 | 0 | 0 | 0 | 0 | 0 | 0 | 0 | 0 | 0 | 2.3 |
| | P3 | 4 | 4 | 0 | 0 | 0 | 0 | 0 | 0 | 0 | 0 | 0 | 0 | 1.7 |
| | P4 | 2 | 0 | 0 | 0 | 0 | 0 | 0 | 0 | 0 | 0 | 0 | 0 | 0.7 |
| 6 hrs | P1 | 4 | 4 | 0 | 0 | 0 | 0 | 0 | 0 | 0 | 0 | 0 | 0 | 1.7 |

-continued

BVDV Inactivation

| Time | | 1 | 2 | 3 | 4 | 5 | 6 | 7 | 8 | 9 | 10 | 11 | 12 | Titer |
|---|---|---|---|---|---|---|---|---|---|---|---|---|---|---|
| | P2 | 4 | 2 | 0 | 0 | 0 | 0 | 0 | 0 | 0 | 0 | 0 | 0 | 1.4 |
| | P3 | 0 | 0 | 0 | 0 | 0 | 0 | 0 | 0 | 0 | 0 | 0 | 0 | 0 |
| | P4 | 0 | 0 | 0 | 0 | 0 | 0 | 0 | 0 | 0 | 0 | 0 | 0 | 0 |
| 24 hrs | P1 | 3 | 0 | 0 | 0 | 0 | 0 | 0 | 0 | 0 | 0 | 0 | 0 | .9 |
| | P2 | 0 | 0 | 0 | 0 | 0 | 0 | 0 | 0 | 0 | 0 | 0 | 0 | 0 |
| | P3 | 0 | 0 | 0 | 0 | 0 | 0 | 0 | 0 | 0 | 0 | 0 | 0 | 0 |
| | P4 | 0 | 0 | 0 | 0 | 0 | 0 | 0 | 0 | 0 | 0 | 0 | 0 | 0 |

These results show that BVDV is somewhat more sensitive than PPV, and that both viruses show increased kill if the samples are incubated for up to 24 hrs before being plated on the cell culture. In earlier experiments without citrate it was necessary to do at least six passes and incubate for 24 hrs to get a complete kill of these very resistant viruses. Also, although the resin used for iodine/iodide capture also has some affinity for citrate, citrate does not appear to interfere with the capture of iodine/iodide. It seems likely that all of the citrate sites become saturated during the first pass. Thereafter iodide merely exchanges for citrate during the capture process.

The above experiment was repeated with a 2000 ml plasma sample with the addition of a 2% sodium citrate sample to the 8% sodium citrate sample. Also, samples were incubated up to 48 hrs prior to plating on the VEPA cell assay.

Results with the iodide/iodine measurement were essentially as before. T

Iodide and Iodine per Pass

| Treatment | Iodide (ppm) | Iodine (ppm) |
|---|---|---|
| Control (2% Citrate) | 0 | 0 |
| (no column treatment) | | |
| Pass 1 (2% Citrate) | 0 | 0 |
| Pass 2 (2% Citrate) | 0 | 0 |
| Pass 3 (2% Citrate) | 0 | 0 |
| Pass 4 (2% Citrate) | 1 | 0 |
| Pass 1 (4% Citrate) | 0 | 0 |
| Pass 2 (4% Citrate) | 0 | 1 |
| Pass 3 (4% Citrate) | 0 | 0 |
| Pass 4 (4% Citrate) | 0 | 0 |

PPV Inactivation (8% Citrate)

| Time | | 1 | 2 | 3 | 4 | 5 | 6 | 7 | 8 | 9 | 10 | 11 | 12 | Titer |
|---|---|---|---|---|---|---|---|---|---|---|---|---|---|---|
| | control | 4 | 4 | 4 | 4 | 4 | 4 | 4 | 4 | 3 | 0 | 0 | 0 | 6.5 |
| 0 hrs | P1 | 4 | 4 | 4 | 4 | 4 | 4 | 4 | 0 | 0 | 0 | 0 | 0 | 5.2 |
| | P2 | 4 | 4 | 4 | 4 | 4 | 3 | 0 | 0 | 0 | 0 | 0 | 0 | 4.4 |
| | P3 | 4 | 4 | 4 | 2 | 0 | 0 | 0 | 0 | 0 | 0 | 0 | 0 | 2.8 |
| | P4 | 4 | 4 | 0 | 0 | 0 | 0 | 0 | 0 | 0 | 0 | 0 | 0 | 1.7 |
| 6 hrs | P1 | 4 | 4 | 4 | 4 | 4 | 0 | 0 | 0 | 0 | 0 | 0 | 0 | 3.8 |
| | P2 | 4 | 4 | 3 | 1 | 0 | 0 | 0 | 0 | 0 | 0 | 0 | 0 | 2.4 |
| | P3 | 4 | 2 | 0 | 0 | 0 | 0 | 0 | 0 | 0 | 0 | 0 | 0 | 1.4 |
| | P4 | 3 | 0 | 0 | 0 | 0 | 0 | 0 | 0 | 0 | 0 | 0 | 0 | 0.9 |
| 24 hrs | P1 | 4 | 2 | 0 | 0 | 0 | 0 | 0 | 0 | 0 | 0 | 0 | 0 | 1.4 |
| | P2 | 0 | 0 | 0 | 0 | 0 | 0 | 0 | 0 | 0 | 0 | 0 | 0 | 0 |
| | P3 | 0 | 0 | 0 | 0 | 0 | 0 | 0 | 0 | 0 | 0 | 0 | 0 | 0 |
| | P4 | 0 | 0 | 0 | 0 | 0 | 0 | 0 | 0 | 0 | 0 | 0 | 0 | 0 |
| 48 hrs | P1 | 4 | 0 | 0 | 0 | 0 | 0 | 0 | 0 | 0 | 0 | 0 | 0 | .7 |
| | | 0 | 0 | 0 | 0 | 0 | 0 | 0 | 0 | 0 | 0 | 0 | 0 | 0 |
| | | 0 | 0 | 0 | 0 | 0 | 0 | 0 | 0 | 0 | 0 | 0 | 0 | 0 |
| | | 0 | 0 | 0 | 0 | 0 | 0 | 0 | 0 | 0 | 0 | 0 | 0 | 0 |

BVDV Inactivation (8% Citrate)

| Time | | 1 | 2 | 3 | 4 | 5 | 6 | 7 | 8 | 9 | 10 | 11 | 12 | Titer |
|---|---|---|---|---|---|---|---|---|---|---|---|---|---|---|
| | control | 4 | 4 | 4 | 4 | 4 | 4 | 0 | 0 | 0 | 0 | 0 | 0 | 5.2 |
| 0 hrs | P1 | 4 | 4 | 4 | 4 | 2 | 0 | 0 | 0 | 0 | 0 | 0 | 0 | 3.5 |
| | P2 | 4 | 4 | 0 | 0 | 0 | 0 | 0 | 0 | 0 | 0 | 0 | 0 | 1.7 |
| | P3 | 4 | 2 | 0 | 0 | 0 | 0 | 0 | 0 | 0 | 0 | 0 | 0 | 1.4 |
| | P4 | 1 | 0 | 0 | 0 | 0 | 0 | 0 | 0 | 0 | 0 | 0 | 0 | 0.4 |

-continued

BVDV Inactivation (8% Citrate)

| Time | | 1 | 2 | 3 | 4 | 5 | 6 | 7 | 8 | 9 | 10 | 11 | 12 | Titer |
|---|---|---|---|---|---|---|---|---|---|---|---|---|---|---|
| 6 hrs | P1 | 4 | 4 | 1 | 0 | 0 | 0 | 0 | 0 | 0 | 0 | 0 | 0 | 1.8 |
| | P2 | 4 | 1 | 0 | 0 | 0 | 0 | 0 | 0 | 0 | 0 | 0 | 0 | 1.1 |
| | P3 | 0 | 0 | 0 | 0 | 0 | 0 | 0 | 0 | 0 | 0 | 0 | 0 | 0 |
| | P4 | 0 | 0 | 0 | 0 | 0 | 0 | 0 | 0 | 0 | 0 | 0 | 0 | 0 |
| 24 hrs | P1 | 4 | 1 | 0 | 0 | 0 | 0 | 0 | 0 | 0 | 0 | 0 | 0 | 1.1 |
| | P2 | 0 | 0 | 0 | 0 | 0 | 0 | 0 | 0 | 0 | 0 | 0 | 0 | 0 |
| | P3 | 0 | 0 | 0 | 0 | 0 | 0 | 0 | 0 | 0 | 0 | 0 | 0 | 0 |
| | P4 | 0 | 0 | 0 | 0 | 0 | 0 | 0 | 0 | 0 | 0 | 0 | 0 | 0 |
| 48 hrs | P1 | 0 | 0 | 0 | 0 | 0 | 0 | 0 | 0 | 0 | 0 | 0 | 0 | 0 |
| | P2 | 0 | 0 | 0 | 0 | 0 | 0 | 0 | 0 | 0 | 0 | 0 | 0 | 0 |
| | P3 | 0 | 0 | 0 | 0 | 0 | 0 | 0 | 0 | 0 | 0 | 0 | 0 | 0 |
| | P4 | 0 | 0 | 0 | 0 | 0 | 0 | 0 | 0 | 0 | 0 | 0 | 0 | 0 |

PPV Inactivation (2% Citrate)

| Time | | 1 | 2 | 3 | 4 | 5 | 6 | 7 | 8 | 9 | 10 | 11 | 12 | Titer |
|---|---|---|---|---|---|---|---|---|---|---|---|---|---|---|
| | control | 4 | 4 | 4 | 4 | 4 | 4 | 4 | 4 | 1 | 0 | 0 | 0 | 6.0 |
| 0 hrs | P1 | 4 | 4 | 4 | 4 | 4 | 4 | 4 | 4 | 0 | 0 | 0 | 0 | 5.9 |
| | P2 | 4 | 4 | 4 | 4 | 4 | 4 | 4 | 4 | 0 | 0 | 0 | 0 | 5.9 |
| | P3 | 4 | 4 | 4 | 4 | 4 | 4 | 4 | 4 | 2 | 0 | 0 | 0 | 6.3 |
| | P4 | 4 | 4 | 4 | 4 | 4 | 4 | 4 | 4 | 0 | 0 | 0 | 0 | 5.9 |
| 6 hrs | P1 | 4 | 4 | 4 | 4 | 4 | 4 | 4 | 4 | 1 | 0 | 0 | 0 | 6.0 |
| | P2 | 4 | 4 | 4 | 4 | 4 | 4 | 4 | 4 | 0 | 0 | 0 | 0 | 5.9 |
| | P3 | 4 | 4 | 4 | 4 | 4 | 4 | 4 | 2 | 0 | 0 | 0 | 0 | 5.6 |
| | P4 | 4 | 4 | 4 | 4 | 4 | 4 | 4 | 0 | 0 | 0 | 0 | 0 | 5.2 |
| 24 hrs | P1 | 4 | 4 | 4 | 4 | 4 | 4 | 4 | 3 | 0 | 0 | 0 | 0 | 5.8 |
| | P2 | 4 | 4 | 4 | 4 | 4 | 4 | 1 | 0 | 0 | 0 | 0 | 0 | 4.7 |
| | P3 | 4 | 4 | 4 | 4 | 4 | 0 | 0 | 0 | 0 | 0 | 0 | 0 | 3.8 |
| | P4 | 4 | 4 | 4 | 4 | 2 | 0 | 0 | 0 | 0 | 0 | 0 | 0 | 3.5 |
| 48 hrs | P1 | 4 | 4 | 4 | 4 | 4 | 4 | 4 | 4 | 0 | 0 | 0 | 0 | 5.9 |
| | | 4 | 4 | 4 | 4 | 4 | 4 | 0 | 0 | 0 | 0 | 0 | 0 | 4.5 |
| | | 4 | 4 | 4 | 4 | 2 | 0 | 0 | 0 | 0 | 0 | 0 | 0 | 3.5 |
| | | 4 | 2 | 0 | 0 | 0 | 0 | 0 | 0 | 0 | 0 | 0 | 0 | 1.4 |

BVDV Inactivation (2% Citrate)

| Time | | 1 | 2 | 3 | 4 | 5 | 6 | 7 | 8 | 9 | 10 | 11 | 12 | Titer |
|---|---|---|---|---|---|---|---|---|---|---|---|---|---|---|
| | control | 4 | 4 | 4 | 4 | 4 | 4 | 3 | 0 | 0 | 0 | 0 | 0 | 5.1 |
| 0 hrs | P1 | 4 | 4 | 4 | 4 | 4 | 4 | 4 | 0 | 0 | 0 | 0 | 0 | 5.2 |
| | P2 | 4 | 4 | 4 | 4 | 4 | 4 | 4 | 0 | 0 | 0 | 0 | 0 | 5.2 |
| | P3 | 4 | 4 | 4 | 4 | 4 | 4 | 3 | 0 | 0 | 0 | 0 | 0 | 5.1 |
| | P4 | 4 | 4 | 4 | 4 | 4 | 4 | 4 | 0 | 0 | 0 | 0 | 0 | 5.2 |
| 6 hrs | P1 | 4 | 4 | 4 | 4 | 4 | 4 | 4 | 0 | 0 | 0 | 0 | 0 | 5.2 |
| | P2 | 4 | 4 | 4 | 4 | 4 | 4 | 4 | 0 | 0 | 0 | 0 | 0 | 5.2 |
| | P3 | 4 | 4 | 4 | 4 | 4 | 4 | 4 | 0 | 0 | 0 | 0 | 0 | 5.2 |
| | P4 | 4 | 4 | 4 | 4 | 4 | 4 | 3 | 0 | 0 | 0 | 0 | 0 | 5.1 |
| 24 hrs | P1 | 4 | 4 | 4 | 4 | 4 | 4 | 4 | 0 | 0 | 0 | 0 | 0 | 5.2 |
| | P2 | 4 | 4 | 4 | 4 | 4 | 4 | 4 | 0 | 0 | 0 | 0 | 0 | 5.2 |
| | P3 | 4 | 4 | 4 | 4 | 4 | 4 | 0 | 0 | 0 | 0 | 0 | 0 | 4.5 |
| | P4 | 4 | 4 | 4 | 4 | 4 | 2 | 0 | 0 | 0 | 0 | 0 | 0 | 4.2 |
| 48 hrs | P1 | 4 | 4 | 4 | 4 | 4 | 4 | 4 | 0 | 0 | 0 | 0 | 0 | 5.2 |
| | P2 | 4 | 4 | 4 | 4 | 4 | 4 | 0 | 0 | 0 | 0 | 0 | 0 | 4.5 |
| | P3 | 4 | 4 | 4 | 4 | 4 | 0 | 0 | 0 | 0 | 0 | 0 | 0 | 3.8 |
| | P4 | 4 | 4 | 4 | 4 | 2 | 0 | 0 | 0 | 0 | 0 | 0 | 0 | 3.5 |

These results show that 8% citrate is dramatically more effective than 2% citrate. The citrate results are relatively paradoxical in that a mixture of citrate and povidone iodine will result in iodide formation presumably from the oxidation of the citrate by the iodine. That would lead one to expect that added citrate would result in blocking of the iodine disinfection as the citrate became oxidized instead of the viral proteins or nucleic acids. One possibility is that the oxidized citrate provides some type of activated intermediate compound that preferentially reacts with the viral components. If this is the case, this intermediate must react solely with nucleic acids since clotting enzyme assays (not shown) demonstrate that the increased citrate concentration does not result in increased protein denaturation. Preliminary results indicate that there may be benefit to preincubating with the citrate prior to addition of iodine or other disinfecting agent.

It is tempting to imagine that there is a unified pathway that explains all of the citrate effects. However it is very difficult to see what this might be. Citric acid is an important part of the Tricarboxylic acid pathway of oxidative metabolism. It is known that citrate is generally rapidly metabolized. Perhaps with bacteria the excess citrate results in some type of metabolic imbalance that make the bacteria especially susceptible to antibiotics and disinfecting dyes. Also, most bacteria have active membrane transport systems for taking up metabolites such as citrate. Perhaps the same transport process that takes up citrate results in an accumulation of antibiotics, dyes or plant products (like the wine polyphenols) in the cell. This might explain the citrate effect on antibiotic resistant microorganisms.

Whatever the mechanism the carboxylic acid effect should be a boon to treatment of drug resistant infections and extending the life of blood fractions such as platelets. Citrate enhancement of antibiotics may work intravenously although the chelating effects of citrate as well as the rapid metabolism of citrate may preclude this use. However, citrate is ideal for use in dialysis procedures to prevent accidental infection. Citrate enhancement is also ideal for use in ointments and other topical applications of anti-infective agents. Citrate enhancement of antibiotics should prove especially effective as antibacterial washes for burn patients. With biologics such as blood and blood products the excess citrate can readily be removed by ion exchange or supplemental calcium can be added to overcome the chelation. In combination with mixed iodine/capture resin columns citrate provides a dramatic improvement in the destruction of contaminating viruses while having a negligible effect on labile proteins. It seems likely that the enhanced killing powers attributed to citrate addition will permit the inactivation of prions and other still mysterious pathogens.

The present invention is described in terms of "citrate" or dicarboxylic acids. The exact mechanism of the present invention is not yet understood. The effect does not seem to extend to all dicarboxylic acids as tartaric acid appears to be relatively ineffective. Other analogous carboxylic acids such as isocitric acid are being investigated.

The following claims are thus to be understood to include what is specifically illustrated and described above, what is conceptually equivalent, what can be obviously substituted and also what essentially incorporates the essential idea of the invention. Those skilled in the art will appreciate that various adaptations and modifications of the just-described preferred embodiment can be configured without departing from the scope of the invention. The illustrated embodiment has been set forth only for the purposes of example and that should not be taken as limiting the invention. Therefore, it is to be understood that, within the scope of the appended claims, the invention may be practiced other than as specifically described herein.

I claim:

1. A method for enhancing the antimicrobial, effectiveness of vancomycin comprising the step of combining the vancomycin with at least 1% by weight citric acid and or salts of citric acid, wherein an effective antimicrobial combination consists essentially of the antibiotic and the citric acid and/or salts of citric acid.

* * * * *